(12) United States Patent
Anderson et al.

(10) Patent No.: US 7,715,927 B1
(45) Date of Patent: May 11, 2010

(54) IMPLANTABLE MYOCARDIAL INFARCTION PATCH HAVING ELECTROACTIVE POLYMER

(75) Inventors: Dave Anderson, Castaic, CA (US); Annapuma Karicherla, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 435 days.

(21) Appl. No.: 11/689,462

(22) Filed: Mar. 21, 2007

(51) Int. Cl.
 *A61N 1/00* (2006.01)
(52) U.S. Cl. ..................................... 607/152
(58) Field of Classification Search .............. 607/152, 607/9
See application file for complete search history.

(56) References Cited

U.S. PATENT DOCUMENTS

| 5,479,352 A * | 12/1995 | Smith ........................ 700/95 |
| 2001/0029348 A1 * | 10/2001 | Willis ........................ 604/20 |
| 2004/0249236 A1 | 12/2004 | Hegde et al. |
| 2006/0217774 A1 | 9/2006 | Mower et al. |

* cited by examiner

*Primary Examiner*—George Manuel
*Assistant Examiner*—Shubatra Narayanaswamy

(57) ABSTRACT

A myocardial infarction patch for placement over a myocardial infarction includes an electroactive polymer (EAP) structure. Varying electricity supplied to the EAP structure causes the patch to expand and contract over the myocardial infarction. The expansion and contraction of the patch can be coordinated with the expansion and contraction of the heart. The electricity is provided to the EAP via a pacemaker, defibrillator, ICD or similar pulse-generating device. Causing the patch to expand and contract against the myocardial infarction can improve the ejection fraction of the heart.

9 Claims, 4 Drawing Sheets

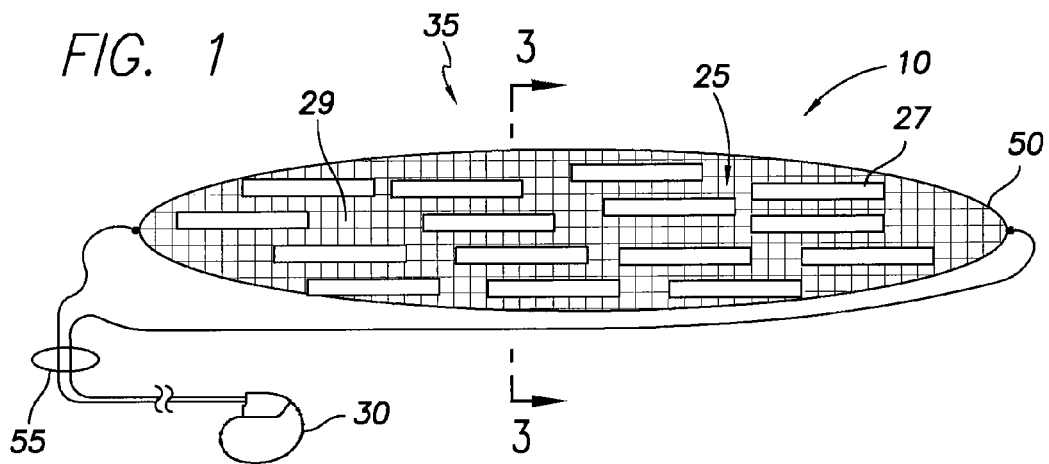
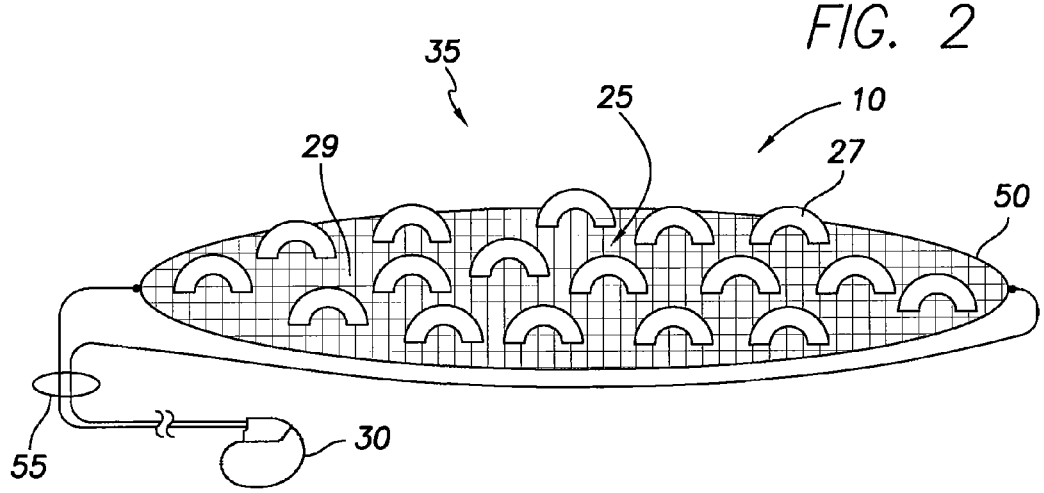
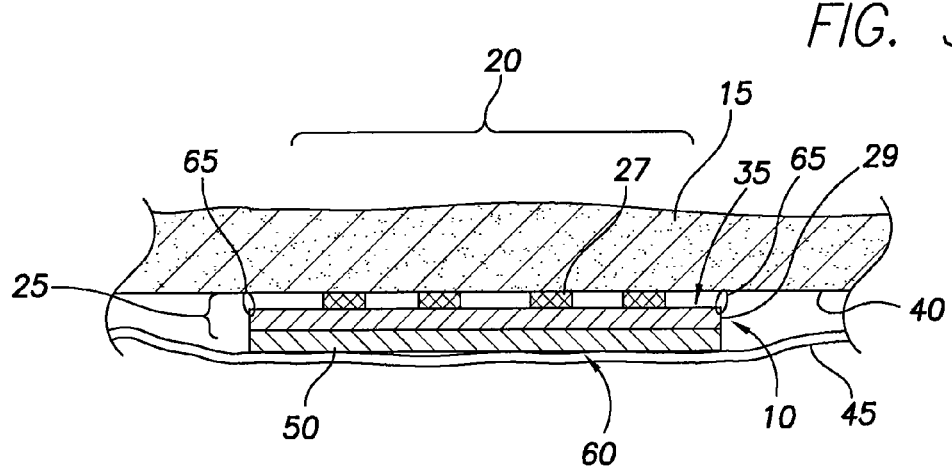

IMPLANTABLE MYOCARDIAL INFARCTION PATCH HAVING ELECTROACTIVE POLYMER

FIELD OF THE INVENTION

The present invention relates to medical apparatus and methods. More specifically, the present invention relates to myocardial infarction patches and methods of treating myocardial infarctions.

BACKGROUND OF THE INVENTION

Placing a surgical patch over a myocardial infarction ("MI") is being researched as a possible route for preventing an infarcted region from rapidly progressing towards heart failure ("HF"). Specifically, it has been suggested that placement of a surgical patch over a MI to contain left ventricle ("LV") mechanical remodeling causes reasonable benefit and possible improvement in ejection fraction ("EF"). The patch reinforces the MI and distresses the entire MI region, thereby allowing the LV to maintain its shape and size and reducing the likelihood of HF.

Tissue in the region of an MI is damaged and has a reduced ability to contract as necessary to take part in the heart's pumping process. Thus, the MI region of the heart has a reduced ability to contribute to the heart's pumping process. Simply placing a surgical patch over a MI does not rectify the loss of pumping force caused by the MI.

There is a need in the art for a MI patch that at least in part rectifies the loss of pumping force caused by a MI. There is also a need in the art for a method of rectifying the loss of pumping force caused by a MI.

SUMMARY

In one aspect, the invention relates to a myocardial infarction patch that includes an electroactive polymer (EAP) structure. The application of electricity to the EAP structure causes the patch to expand and/or contract.

In another aspect, the invention relates to a method of using the aforementioned myocardial infarction patch to treat a heart having a myocardial infarction. The method includes placing the patch over the myocardial infarction, and varying electricity supplied to the EAP structure, thereby causing the patch to expand and contract over the myocardial infarction. Expansion and contraction of the patch may be coordinated with the expansion and contraction of the heart. The electricity may be provided by a source within a pacemaker, defibrillator or ICD. Providing the patch over the myocardial infarction can reduce or stop the adverse progression of the infarction. Additionally, causing the patch to expand and contract over the myocardial infarction can provide some improvement with respect to the ejection fraction of the heart.

While multiple embodiments are disclosed, still other embodiments of the invention will become apparent to those skilled in the art from the following detailed description, which shows and describes illustrative embodiments of the invention. As will be realized, the invention is capable of modifications in various aspects, all without departing from the spirit and scope of the invention. Accordingly, the drawings and detailed description are to be regarded as illustrative in nature and not restrictive.

BRIEF DESCRIPTION OF THE DRAWINGS

FIG. 1 is a diagrammatic view of an electroactive polymer ("EAP") side of a myocardial patch including an EAP structure having a plurality of EAP elements in an expanded state.

FIG. 2 is the same view depicted in FIG. 1, except the EAP elements are in a contracted state.

FIG. 3 is a cross-section through the patch taken along section line 3-3 of FIG. 1, wherein the patch is positioned over a myocardial infarction and between an epicardial surface of the heart and a pericardial sac.

DETAILED DESCRIPTION

Figure 5:
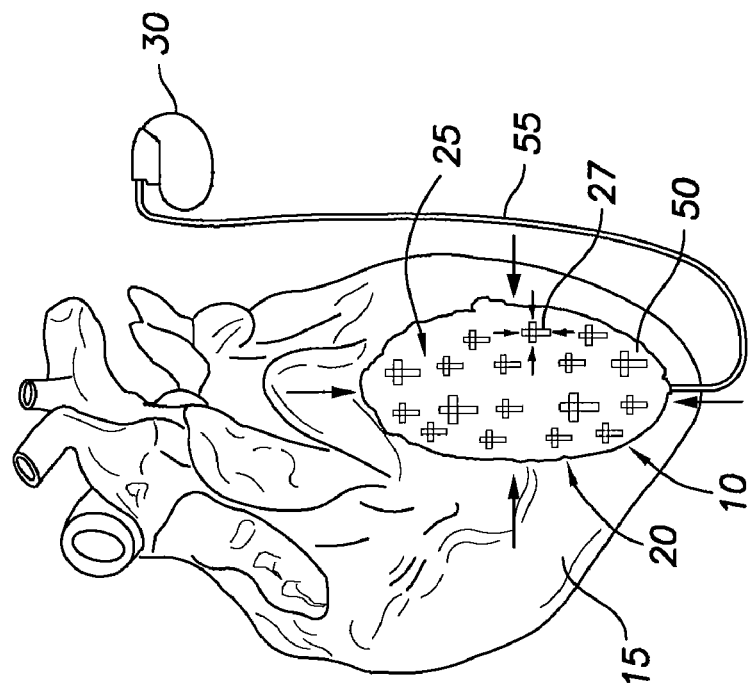
FIG. 5 is the same view as FIG. 4, except the patch and EAP elements are in a contracted state.

A myocardial infarction patch 10 and a method of treating a heart 15 having a myocardial infarction ("MI") 20 are disclosed herein. In one embodiment, the patch 10 includes an electroactive polymer ("EAP") structure 25 having a plurality of EAP elements 27. In use, the patch 10 is located over a MI 20 and coupled to an electrical power source 30 such as a pacemaker, defibrillator, ICD or other type of pulse generator. Varying electricity applied to the EAP structure 25 from the power source 30 causes the EAP elements 27 to expand and contract, which in turn causes the patch 10 to expand or contract over the MI 20. The expanding and contracting of the patch 10 can be coordinated with the expanding and contracting of the heart 15. Thus, the patch 10 can be used to supply a pumping force in the area of the MI 20 and improve the ejection fraction of the heart.

Figure 4:
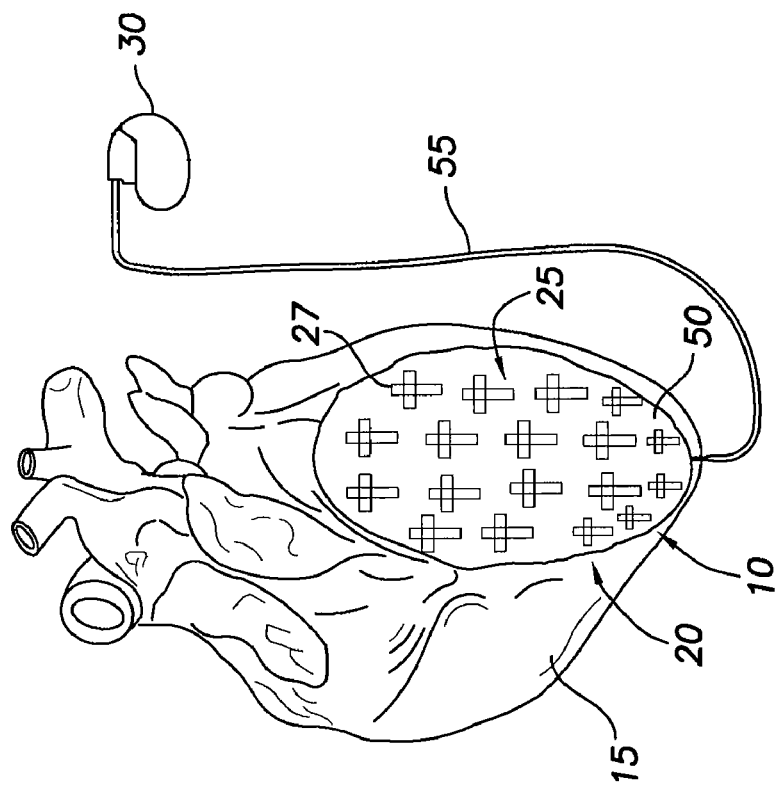
FIG. 4 is a left ventricle side view of a heart with patch and EAP elements in an expanded state, wherein the EAP elements are portrayed as being visible for the sake of discussion, but would actually be hidden in reality as can be understood from FIG. 3.

For a discussion regarding the myocardial infarction patch 10, reference is made to FIGS. 1-5. FIG. 1 is a diagrammatic view of an EAP side 35 of a patch 10, wherein the EAP structure 25 and EAP elements 27 are expanded. FIG. 2 is the same view depicted in FIG. 1, except the EAP structure 25 and EAP elements are contracted. FIG. 3 is a cross-section through the patch 10 as taken along section line 3-3 of FIG. 1, wherein the patch 10 is positioned over a MI 20 and between an epicardial surface 40 of the heart 15 and a pericardial sac 45. FIG. 4 is a left ventricle side view of a heart 15 with patch 10 with the EAP elements 27 in an expanded state, wherein the EAP elements 27 are portrayed as being visible for the sake of discussion, but would actually be hidden in reality as can be understood from FIG. 3. FIG. 5 is the same view as FIG. 4, except the patch 10 and EAP elements 27 have contracted.

As shown in FIGS. 1 and 2, in one embodiment, the patch 10 includes a patch substrate 50, an electrically conductive EAP 25 structure mounted on the patch substrate 50, and electrical conductors 55 electrically connecting the EAP 25 structure to a power source 30. In one embodiment, the EAP 25 structure includes a plurality of EAP elements 27 distributed to a greater or lesser extent across the EAP side 35 of the patch substrate 50.

With reference to FIGS. 1 and 2, in one embodiment, the EAP elements 27 are linear strips oriented such that they all extend in generally the same direction, thereby causing the patch 10 to expand and contract along one line of action.

As illustrated in FIGS. 4 and 5, in another embodiment, the EAP elements 27 may be oriented such that they cross or weave over each other or, alternatively, simply extend in different directions without contacting each other. Accordingly, a first substantial number of the EAP elements 27 may generally extend in a first direction, a second substantial number of EAP elements 27 may generally extend in a second direction, and so forth. Such an arrangement allows the patch 10 to expand (FIG. 4) or contract (FIG. 5) along two or more lines of action.

With reference to FIG. 3, in one embodiment, the patch substrate 50 has a smooth side 60 and an EAP side 35 that carries the EAP structure 25. In one configuration, the patch substrate 50 is a sheet formed of a nonconductive polymer material such as silicone rubber, polyurethane, polyester, polypropylene or other biocompatible and biostable polymers. The nonconductive polymer layer lends robustness and body to the patch substrate 50 and allows for better handling characteristics of the patch 10.

As shown in FIG. 3, the EAP structure 25 includes a conductive structure 29 with a plurality of EAP elements 27 mounted to, or formed thereon. When the EAP material of choice is Ionomeric Polymer Metal Composites, Polypyrrole or Polyaniline (conductive polymers from the Ionic EAP class), the conductive structure 29 is a conductive layer of material. In one embodiment, the conductive layer 29 is formed of an actuable polymer material such as conductive actuatable polymers like Ionomeric Polymer Metal Composites, Polypyrrole or Polyaniline (Ionic EAP class), or etc. In this configuration, the actuable conductive layer 29 and actuable EAP elements 27 combine to provide the actuation feature of the patch 10 with the actuable conductive layer 29 also functioning as a conduit for electricity to the EAP elements 27, via the conductive wires 55.

In another embodiment, the conductive layer 29 is formed of a conductive but non-actuatable, i.e., non-expanding/contracting material, such as gold or platinum. In this configuration, the EAP elements 27 provide the actuation feature of the patch 10, while the conductive layer merely functions as a conduit for electricity to the EAP elements 27.

As explained further below with reference to FIG. 7, when the EAP material of choice is an electronic EAP material, the conductive structure 29 includes a non-conductive layer of material with electrically conductive traces for connecting the conductive wires 55 to the EAP elements 27.

In one embodiment, an additional layer (not shown) may be added to the pericardial-sac side 60 of the EAP patch 10. This additional layer is biodegradable over time and formed from such materials as cellulose or a hydrogel based material that prevents friction between the pericardial sac 45 and the EAP patch 10. In an alternate embodiment, a non-biodegradable material such as ePTFE (Gore-Tex) could also be used As depicted in FIG. 3, the patch 10 is positioned over the MI 20 such that the EAP side 35 extends against the epicardial surface 40, and the smooth side 60 extends against the pericardial sac 45. In one embodiment, the EAP elements 27 are anchors that assist in keeping securing the patch 10 positioned over the MI 20 and engaged with the epicardial surface 40.

As an alternate or additional means of securing the patch 10 in place relative to the epicardial surface, either the EAP structure 25 or the patch substrate 50 may be formed to include a weaved or mesh material that provides for tissue in-growth. To further secure the EAP side 35 to the epicardial surface 40, a tissue adhesive 65 (e.g., gelatin resorcinol formaldehyde ("GRF") based glue, polyethylene glycol derived glue, cyanoacrylate, glutaraldehyde based glue, or fibrin based glue), a suture 65, or other anchoring mechanism 65 is used between the EAP side 35 and the epicardial surface 40.

Figure 6:
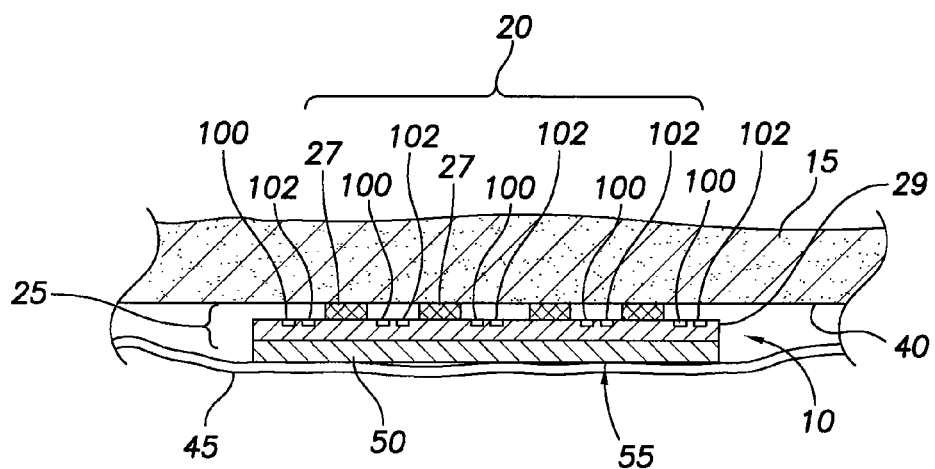
FIG. 6 is the same cross-section depicted in FIG. 3, except the patch includes glue cells with glue for adhering the patch to the epicardial surface.

With reference to FIG. 6, in another configuration, the EAP patch 10 includes glue cells 100, 102 for dispensing glue 105 to adhere the patch to the epicardial surface 40. In one embodiment, the glue cells 100, 102 are incorporated within the patch 10 and are small, micron sized cells.

The glue contained in the cells 100, 102 may be a two part adhesive that cures upon application of the second adhesive part to the first adhesive part. As shown in FIG. 6, in one arrangement, the cells 100, 102 are paired or otherwise grouped such that one glue cell 100 contains the first adhesive part and another nearby glue cell 102 contains the second adhesive part. An electrical pulse of a first frequency is applied to the patch 10, causing the first glue cells 100 to release the first adhesive part contained therein. The first frequency is unique to the first glue cells 100 in that only the first glue cells 100 will actuate to dispense their contents (i.e., the first adhesive part). The electrical pulse of the first frequency will not actuate the EAP elements 27 or the second glue cells 102.

An electrical pulse of a second frequency different from the first frequency is applied to the patch 10 subsequent to or at the same time as the electrical pulse of the first frequency. The second frequency is unique to the second glue cells 102 in that only the second glue cells 102 will actuate to dispense their contents (i.e., the second adhesive part). The electrical pulse of the second frequency will not actuate the EAP elements 27 or the first glue cells 100.

In an alternate embodiment, the first and second glue cells 100, 102 may be actuated by the same pulse frequency. However, the pulse frequency for actuating the glue cells 100, 102 will not actuate the EAP elements 27.

Regardless of whether the first adhesive part and second adhesive part are released from the cells 100, 102 separately or generally simultaneously, the second adhesive part encountering the first adhesive part causes the glue to cure and adhere the patch 10 in position in a matter of minutes with substantially reduced mess and difficulty.

In one embodiment, the first and second glue cells 100, 102 are formed in the conductive layer 29 of the EAP structure 25. The glue cells 100, 102 may be pockets or areas of EAP material that can be actuated by an electrical pulse to free their respective adhesive contents. In one configuration, the glue cells 100, 102 contain the components to form a fibrin based adhesive. For example, one plurality of glue cells 100 contains fibrinogen, and the other plurality of glue cells 102 contains thrombin. When the glue cells 100, 102 are actuated via an electrical pulse to free their respective contents, the contents (i.e., the fibrinogen and thrombin) come into contact with each other to form a clot or, in other words, the fibrin based adhesive. The speed of clot formation is generally a function of the thrombin concentration.

Figure 7:
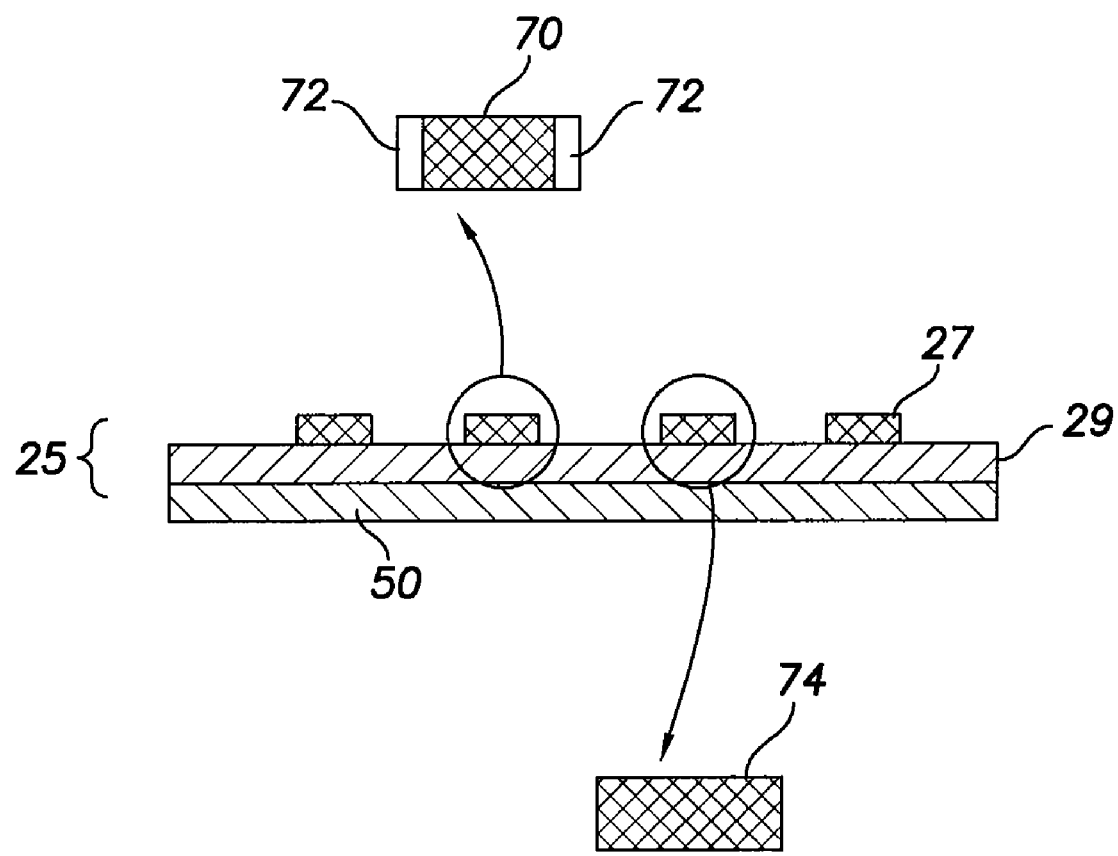
FIG. 7 is a cross section of a patch depicting two possible configurations of EAP elements included in an EAP structure.

With reference to FIG. 7, in one embodiment, the EAP elements 27 are formed of an electronic EAP material 70 such as ferroelectric polymers or dielectric EAPs such as silicone or polyurethane with electrodes 72 mounted on either side. The conductive structure 29 includes electrical traces (not shown) for applying establishing electrical potentials across the electrodes 72. The application of such potentials to the electrodes 72 induces an electrical force that squeezes the material 70 causing expansion between the electrodes in that plane. In other embodiments, the EAP material is electro restrictive graft elastomers such as poly (vinylidene-fluoridetri fluoro ethylene), or etc. Electronic EAP material is advantageous in that it can generate large forces, e.g., a few Newtons (N). The large electrical requirements, e.g., greater than 500 volts, of electronic EAP material can be delivered via an ICD or similar pulse-generating device 30.

With continued reference to FIG. 7, in another embodiment, the EAP elements 27 are formed of an ionic EAP material 74, such as polypyrrole ("Ppy"), Polyaniline, polythiophenes, or etc. Ionic EAP material is advantageous in that it has small electrical requirements, e.g., less than 2 volts. Ionic EAP material generates small forces on the order of milli-Newtons (mN), but the combined or cumulative forces of a substantial number of EAP elements 27 are sufficient to cause adequate contraction/expansion of the patch 10. Other classes of Ionic EAP materials such as electro rheological fluids, Ionomeric Polymer Metal Composites, and Ionic gels can also be utilized for making the actuator part of the patch.

Figure 8:
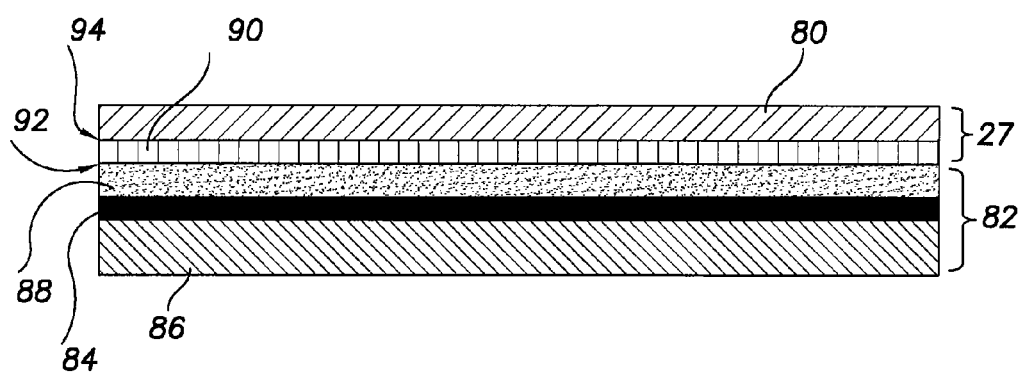
FIG. 8 is a cross section taken through an EAP element formed by employing thin film technology.

With reference to FIG. 8, electroplating and electro deposition methods may be used to make ionic EAP (conductive polymers) like Polypyrrole. In an exemplary manufacturing method, thin film technology (i.e., a number of thin layers are stacked on top of each other and patterned using techniques such as photolithography, etching, electroplating, spin coating, etc.) is used to form the EAP elements 27. A layer of EAP material 80 is deposited on a film structure 82. The film structure 82 includes a layer of titanium foil 84 having a thickness of 1-100 microns on a dummy structure 86. An optional layer of polyurethane 88 having a thickness of 1-10 microns may be included on the titanium foil 84. The polyurethane lends some robustness to the film structure 82.

Before deposition of the EAP material 80, a layer of gold 90, having a thickness of approximately 100 nm is coated onto the polyurethane 88, if present, or directly on the titanium foil 84 using thermal evaporation. The gold layer 90 provides a conducting surface onto which other materials can be deposited. The gold film 90 also protects the polyurethane 88 from chemicals used later on in the process. To promote polyurethane-gold adhesion, a very thin Cr layer 92 may be introduced between the two.

The EAP material 80 is applied to the gold layer 90. In one embodiment, the EAP material is electroactive polymer polypyrrole (PPy). PPy is electro polymerized from a solution containing pyrrole monomer and a salt called NaDBS. To improve Au-PPy adhesion, an adhesion layer 94 may be added before electropolymerization. A thin PPy coating can be applied to all exposed Au areas.

After EAP deposition, the film structure 82 may be removed via etching leaving an EAP element 27 having a layer of gold 88 and a layer of EAP material 80. With reference to FIG. 7, the EAP structure 27 is mounted on the conductive structure 29. It should be understood that the foregoing is but one way of forming EAP elements. Furthermore, as alternatives to forming individual EAP elements and mounting them to the conductive structure, several EAP elements may be formed in a desired arrangement using well known masking techniques and the arrangement mounted to the conductive structure, or the EAP elements may be directly formed on a patch substrate that is coated with a layer of conductive material.

As previously mentioned, the EAP side 35 of the patch 10 is secured to the epicardial surface 40, and pericardial sac 45 is able to slide or displace relative to the smooth side 60 of the patch 10. Electricity supplied to the EAP structure 25 via the power supply 30 is varied to cause the EAP elements 27 to expand, as shown in FIG. 4, and contract, as shown in FIG. 5. The expansion/contraction of the EAP elements 27, in turn, cause the patch 10 to move between an expanded state, as shown in FIG. 4, and a contracted state, as shown in FIG. 5. Because the EAP side of the patch 10 is secured to the epicardial surface 40, expanding and contracting the patch 10 causes the heart wall to expand or contract at the location of the patch 10.

Where the patch 10 is located over a MI 20 in the heart wall, the expanding and contracting patch 10 can cause the expansion and contraction of the heart wall forming the MI 20, thereby improving ejection fraction for the heart 15. A pacemaker or ICD 30 can be used to coordinate contraction/expansion of the patch 10 with the expansion/contraction of the heart 15 such that the heart wall having the MI 20 expands/contracts in correct rhythm with the rest of the heart 15. In other words, the patch 10 will expand/contract with each expansion/contraction of the heart 15 and force the MI 20 to expand/contract with each expansion/contraction of the heart 15. Thus, pumping pressure of the heart 15 increases as the patch 10 at least partially compensates for the loss of pumping pressure caused by the MI 20.

In one embodiment, one or more of the EAP elements 27 can be used for pacing, defibrillation and/or sensing heart tissue in contact with the EAP elements 27. Where a large number of the EAP elements 27 are used for pacing, etc., the patch 10 can serve as a large surface electrode for stimulating and sensing viable tissue.

In one embodiment, the pulse generator 30 is a small (e.g. approximately one to two centimeters in diameter) battery 30 mounted remotely from the patch 10, as traditionally done with implantable pulse generators 30. In other embodiments, the battery 30 is mounted on or otherwise incorporated into the patch 10 itself, thereby allowing the patch to be self contained and self powered. In some embodiments, regardless of whether the battery is mounted remotely or incorporated into the patch, the battery 30 is a bioelectric battery 30 that is regenerated using resources available in the blood pool or tissue. An example of such a bioelectric battery 30 is provided in U.S. Provisional Patent Application 60/071,602 entitled Bioelectric Battery for Implantable Device Applications, which was filed on Dec. 22, 2006 and is hereby incorporated by reference in its entirety into this Detailed Description.

The above described patch 10 is advantageous because it not only reinforces and de-stresses the MI 20 to prevent further ventricular remodeling, it also causes the MI area of the heart wall to expand/contract, thereby improving the ejection fraction of the heart 15 relative to what it would be without the forced expansion/contraction caused by the patch 10. Electrical stimulation capability and device stimulated contraction/expansion of infarcted regions (or possibly even ischemic regions) may potentially curtail disease progression, including heart failure progression. Furthermore, the patch 10 allows for pacing, defibrillation and/or sensing at the MI area of the heart wall.

Although the present invention has been described with reference to preferred embodiments, persons skilled in the art will recognize that changes may be made in form and detail without departing from the spirit and scope of the invention.

What is claimed is:

1. A myocardial infarction patch comprising:
   an electroactive polymer (EAP) structure; and
   a plurality of cells carried by the EAP structure,
   wherein at least one of the plurality of cells contains a first adhesive part and at least one other of the plurality of cells contain a second adhesive part, the at least one and the at least other of the plurality of cells configured to release the first and second adhesive parts respectively upon receiving at least one electrical signal, the first and second adhesive parts comprising a two-part adhesive configured to cure when the first and second adhesive parts are combined.

2. The patch of claim 1 wherein the EAP structure comprises a plurality of EAP elements and a conductive structure on which the plurality of EAP elements are located and the plurality of cells are incorporated in the conductive structure.

3. The patch of claim 2 wherein the conductive structure comprises a layer of conductive material.

4. A method of treating a heart having a myocardial infarction, the method comprising:
   placing a patch over the myocardial infarction, wherein the patch includes an electroactive polymer (EAP) structure and at least one cell carried by the EAP structure;
   actuating the at least one cell via an electrical signal to cause the at least one cell to release a substance contained in the at least one cell; and
   varying electricity supplied to the EAP structure, thereby causing the patch to expand and contract over the myocardial infarction.

5. The method of claim 4 wherein the substance comprises an adhesive and actuating the at least one cell causes the at least one cell to release the adhesive between the patch and the myocardial infarction.

6. The method of claim 4 wherein the at least one cell comprises a plurality of cells, the plurality of cells including at least one first cell containing a first adhesive part and at least one second cell containing a second adhesive part, the first and second adhesive parts comprising a two-part adhesive configured to cure when the first and second adhesive parts are combined, the method further comprising actuating the plurality of cells via at least one electrical signal to cause the at least one first cell and the at least one second cell to respectively release the first and second adhesive parts between the patch and the myocardial infarction.

7. The method of claim 6 wherein actuating the plurality of cells via at least one electrical signal comprises supplying a first electrical signal at a first frequency to cause the at least one first cell to release the first adhesive part and supplying a second electrical signal at a second frequency, different from the first frequency, to cause the at least second cell to release the second adhesive part.

8. The method of claim 7 wherein supplying the second electrical signal at the second frequency is subsequent to supplying the first electrical signal at the first frequency.

9. A method of treating a heart having a myocardial infarction, the method comprising:
   placing a patch over the myocardial infarction, wherein the patch includes an electroactive polymer (EAP) structure and at least one cell carried by the EAP structure;
   actuating the at least one cell via an electrical signal to cause the at least one cell to release a substance contained in the at least one cell; and
   varying electricity supplied to the EAP structure, thereby causing the patch to expand and contract over the myocardial infarction;
   wherein the electrical signal actuating the at least one cell does not actuate the EAP structure.

* * * * *